United States Patent [19]

Mondelo et al.

[11] Patent Number: 4,929,440

[45] Date of Patent: May 29, 1990

[54] PROCESS FOR THE PREPARATION OF (−) EBURNAMENIN-14-(15H)-ONE RESINATES

[75] Inventors: Fernando C. Mondelo; Maria T. M. Ferrero, both of Madrid, Spain

[73] Assignee: Covex, S.A., Madrid, Spain

[21] Appl. No.: 171,672

[22] Filed: Mar. 22, 1988

Related U.S. Application Data

[62] Division of Ser. No. 926,561, Oct. 31, 1986, abandoned.

[30] Foreign Application Priority Data

Nov. 8, 1985 [ES] Spain .................................. 548735

[51] Int. Cl.$^5$ ............................................ A61K 31/795
[52] U.S. Cl. .................................... 424/79; 424/451; 424/464; 525/332.2
[58] Field of Search ............... 525/328.5, 332.2, 333.5; 424/79

[56] References Cited

U.S. PATENT DOCUMENTS 4,359,555  11/1982  d'Hondt .......................... 525/358
4,510,128  4/1985   Khanna ............................ 424/79

Primary Examiner—Christopher Henderson
Attorney, Agent, or Firm—Ladas & Parry

[57] ABSTRACT

A process for the preparation of (−)eburnamenin-14-(15H)-one resinates having improved pharmacological properties.

These resinates are prepared by reacting phosphate or any addition salts of (−)eburnamenin-14-(15H)-one with an alkali metal sulphonate type cationic resin, in a polar solvent for 10 hours at 50° C. under stirring.

2 Claims, No Drawings

PROCESS FOR THE PREPARATION OF (−) EBURNAMENIN-14-(15H)-ONE RESINATES

This is a divisional of co-pending application Ser. No. 926,561 filed on Oct. 31, 1986 now abandoned.

The process according to the invention has been conceived for the production of (−)Eburnamenin-14(15H)-one preparations of a prolonged medical action, corresponding to the general formula I:

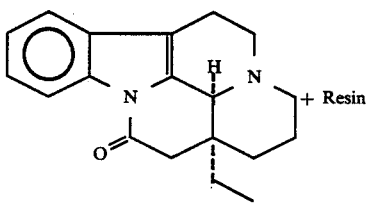

hereinafter as (−)Eburnamenin-14(15H)-one resinates.

(−)Eburnamenin-14(15H)-one and the addition salts thereof, such as phosphate, are very important compounds from a pharmaceutical point of view, especially in geriatrics, being used for the treatment of brain circulation and brain hypoxia problems and of the consequences thereof.

U.S. Pat. No. 4,369,175 describes a method whereby preparations of another alkaloid related to I, the vincamin, of general formula II, with a prolonged action.

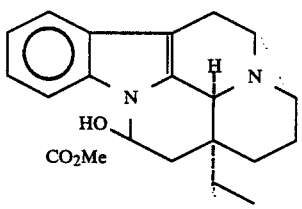

In said patent, reference is made to a series of vincamin addition salt preparations, of a low stability and less efficient than preparations with ionic, preferably cationic, exchanger resins, which allow the production of prolonged action pharmaceutical preparations which do not depend on the substrate used, but on the active agent.

The mechanism for obtaining the retarded action in this kind of preparations, is based on the suspension of the active product in a lipoid liquid or on the encapsulation thereof in a polyethylene glycol, cellulose derivatives, polyvinyl acetate, etc. matrix. Thus, the granulated preparations can be used for the manufacture of tablets, capsules or syrups of oral administration.

In the same way, (−)Eburnamenin-14(15H)-one can be used for the manufacture of retarded action active preparations by fixing the addition salts thereof to cationic resins, this being the method used in the present process.

The use of cationic exchanger resins for the obtention of prolonged effect pharmaceutical preparations has been sometimes proposed. For instance, patent DE 1,045,599 describes the manufacture of prolonged action amine preparations by reacting the amines in way of addition salts with cationic exchanger resins with sulfonic groups, particularly compounds of the polyvinyl or aryl sulfonates type, being copolymerized with a 3–12% of divinyl benzene.

On the other hand, it has been seen that the resinates being obtained from amines in way of free bases with an anionic resin are not stable and, therefore, the preparations of process of the present invention refer to the manufacture of resinates constituted by a eburnamenin-14(15H)-one salt, especially chlorhydrate and phosphate, with a cationic exchanger resin of the polyvinyl or aryl sulfonate type, copolymerized with a 3–12% of divinyl-benzene.

The reaction is carried out in aqueous solution at a temperature between 30° and 50° C., for 8 to 10 hours, after which the resin is filtered off and dried at 30° C. of temperature until constant weight, and the product is thus ready for its encapsulation or for any other later treatment. The particle size of the resins used may range between 50 and 1000 μm, being preferred those sizes between 100 and 300 μm.

The compounds obtained as (−)eburnamenin-14-(15H)-one resinates are very stable and can be stored with no visible physical-chemical changes for periods of time from six months up to one year.

The (−)eburnamenin-14-(15H)-one resinates or the citrate can be orally administered, as well as the pure base, under tablets, capsules, aromatized syrups or drops (suspensions). Each dose may contain 60 mg of active element and it can be reduced as convenient for the specific treatment.

A better comprehension of the process according to the invention will be achieved with the following non-limitative examples.

EXAMPLE 1

100 mg of IRP-69M amberlite (styrene co-polymer with a 8% of divinyl-benzene) with particle size lesser than 75 μm are suspended in 500 ml of hydrochloric acid 2N and the mixture is vigorously stirred at 40° C. for 2 hours. The supernatant solution is poured and the resin washed with three portions of deionized water of 50 ml each. Afterwards, 500 ml of a sodium hydroxide solution 2N is added to the resin. The suspension is stirred at 40° C. for 6 hours, after which it is filtered and washed with deionized water in a sufficient amount until reaching a filtration water pH of 5. The process is completely repeated for another two times. Finally, the resin is dried under vacuum until constant weight at 50° C.

8.3 g of (−)eburnamenin-14(15H)-one phosphate are suspended in 100 ml of deionized water and further added 36.5 g of IRP-69M amberlite, previously purified according to the description of the above paragraph. The resulting suspension is vigorously stirred at 40° C. for 18 hours, after which the resin is filtered under vacuum, the obtained resinate dried at 50° C. and under vacuum until constant weight, thereby obtaining 44.0 g of resinate. The obtained dry resinate contains an (−)eburnamenin phosphate percentage in weight of the 22%.

EXAMPLE 2

11.5 g of (−)eburnamenin-14-(15H)-one chlorihydrate are suspended in 100 ml of deionized water and are further added 36.5 g of IRP-69M amberlite, previously purified according to Example 1. The resulting suspension is vigorously stirred at 50° C. for 10 hours, after which the resin is filtered under vacuum. The obtained resinate is dried at 50° C. under vacuum until constant weight, thereby obtaining 44 g of resinate. The dry resinate contains an (—)eburnamenin chlorhydrate percentage in weight of the 22%.

EXAMPLE 3

5 g of (—)eburnamenin resinate are suspended in 100 ml of water containing a conventional flavour excipient, thereby forming a potion or suspension so that 5 ml thereof (one spoonful) contain approximately the necessary amount for a dose of the compound each 12 hours, a 24 hour period being expired, and a total administered and usable amount of mg of 45 to 50 mg of (—)eburnamenin, depending on the original salt used.

The amendments which might be introduced in the described object and which do not alter the characteristic essence thereof, will be understood as included under the protection field of the following claims.

We claim:

1. The (—)eburnamenin-14-(15H)-one resinates, wherein the cationic resin is selected from polyvinyl or aryl sulfonates copolymerized with 3–12 divinyl benzene.

2. The (—)eburnamenin-14-(15H)-one resinates, wherein the cationic resin comprises a styrene copolymer copolymerized with divinyl benzene.

* * * * *

UNITED STATES PATENT AND TRADEMARK OFFICE
CERTIFICATE OF CORRECTION

PATENT NO. : 4,929,440

DATED : May 29, 1990

INVENTOR(S) : Mondelo et al.

It is certified that error appears in the above-identified patent and that said Letters Patent is hereby corrected as shown below:

ON TITLE PAGE:

Page 1, Column 1, Item [54], delete "PROCESS FOR THE PREPARATION OF"

Page 1, Column 1, Item [75] Inventors: delete "C." and substitute --Calvo--. delete "M." and substitute --Manresa--.

Page 1, Column 2, Item [57] delete "A PROCESS FOR THE PREPARATION OF"

Signed and Sealed this

Twenty-second Day of October, 1991

*Attest:*

HARRY F. MANBECK, JR.

*Attesting Officer*     *Commissioner of Patents and Trademarks*